United States Patent [19]

Okada et al.

[11] Patent Number: 5,603,755
[45] Date of Patent: Feb. 18, 1997

[54] PREVENTIVE AAGENT FOR FOULING ORGANISMS

[75] Inventors: Hideo Okada; Atsuya Mochizuki; Hideo Ohi, all of Shizuoka-ken, Japan

[73] Assignee: Ihara Chemical Industry Co., Ltd., Tokyo, Japan

[21] Appl. No.: 564,270

[22] PCT Filed: Apr. 28, 1995

[86] PCT No.: PCT/JP95/00852

§ 371 Date: Dec. 28, 1995

§ 102(e) Date: Dec. 28, 1995

[87] PCT Pub. No.: WO95/29591

PCT Pub. Date: Nov. 9, 1995

[30] Foreign Application Priority Data

Apr. 28, 1994 [JP] Japan .................................... 6-114617

[51] Int. Cl.$^6$ .................................................. A01N 43/78
[52] U.S. Cl. ..................... 106/18.33; 514/365; 523/122; 523/177; 548/204; 548/205
[58] Field of Search ........................... 514/365; 548/204, 548/205; 106/18.33; 523/122, 177

[56] References Cited

U.S. PATENT DOCUMENTS 4,320,125  3/1982  Puttner et al. .......................... 514/365
4,626,543  12/1986  Kollmeyer ............................. 514/365

FOREIGN PATENT DOCUMENTS 50-70524  6/1975  Japan .
55-154962  12/1980  Japan .
61-180778  8/1986  Japan .

*Primary Examiner*—Anthony Green
*Attorney, Agent, or Firm*—Oblon, Spivak, McClelland, Maier & Neustadt, P.C.

[57] ABSTRACT

The present invention provides a preventive agent for fouling organisms, which comprises, as an effective ingredient, at least one compound selected from compounds represented by general formula (1)

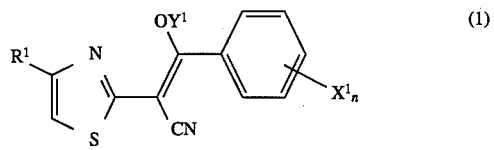

(1)

[wherein $R^1$ is a lower alkyl group, or a phenyl group which may be substituted with a halogen atom(s) and/or a lower alkyl group(s); each $X^1$ is a halogen atom; n is an integer of 1–5; when n is 2 or more, $X^1$s may be the same or different; and $Y^1$ is a hydrogen atom or a group —Z—$Y^2$ (Z is a carbonyl group or a sulfonyl group, and $Y^2$ is a substituted or unsubstituted aryl group or a lower alkyl group], or salts thereof. The present preventive agent for fouling organisms, which contains a compound(s) other than organotin compounds as an effective ingredient, has high safety, prevents the settlement of fouling organisms to ships, in-water structures, fishing nets, etc. at a low effective ingredient content, and exhibits an antifouling effect stably over a long period of time.

13 Claims, No Drawings

PREVENTIVE AAGENT FOR FOULING ORGANISMS

TECHNICAL FIELD

The present invention relates to a preventive agent for fouling organisms, used for the prevention of settlement and propagation of fouling organisms to and on ship hills, fishing nets, in-sea-water facilities (e.g. buoys), in-water structures (e.g. part of dam facilities), feed pipes of cooling water for condenser used in steam power plant or for heat exchanger used in petrochemical plant, etc.

BACKGROUND ART

Shells and algae such as barnacles, oysters, mussels, hydroids, tube worms, bryozoans, tunicates, bryozoans (Ex. Bugula), sea weeds (Ex. Ulva), sea weeds (Ex. Enteromorpha), sea weeds (Ex. Ectocarpus) and the like settle to and propagate on ship hills, in-sea-water facilities (e.g. buoys), in-water structures (e.g. part of dam facilities), feed pipes of cooling water for condenser used in steam power plant or for heat exchanger used in petrochemical plant, etc. (these parts and facilities are in constant contact with water), fishing nets for cultivation or for fixed net fishing, etc., when these parts, facilities and materials have not been subjected to any treatment. These fouling organisms invite increased resistance of water supply and reduced thermal conductivity, and bring about disadvantages such as reduced function of facility and the like. In fishing nets, the settlement of the above-mentioned organisms causes stopping-up of meshes and resultant oxygen shortage, scratching of fish (this reduces the commercial value of fish), and infection of fish with diseases caused by microbes, etc. In order to prevent the settlement and propagation of such sea-water or pure-water fouling organisms, antifouling agents containing an organotin compound as an effective ingredient have been used heretofore. With antifouling agents containing an organotin compound or the like, however, there have recently arisen social problems that environments such as rivers, ocean and the like are polluted and further that said agents give harm to human bodies via fish. Hence, a regulation has been established on the use of organotin compounds, and the use and production of said organotin compounds are under mandatory control.

Meanwhile, organic compounds other than organotin compounds have been studied as an antifouling agent for the same purpose. However, preventive agents for fouling organisms, containing conventional organic compounds have not been satisfactory in antifouling property.

It is an object of the present invention to solve the above-mentioned problems and provide a preventive agent for fouling organisms, containing, as an effective ingredient, an organic compound other than organotin compounds, having high safety and exhibiting a high antifouling effect at a low dosage.

In order to achieve the above object, the present inventors made a study on the preventive activities of various organic compounds for fouling organisms. As a result, the present inventors unexpectedly found out that some of 3-oxopropionitrile derivatives have high preventive activities for fouling organisms and that the use of said compound can achieve the above object and can provide a preventive agent for fouling organisms, having a high antifouling effect. The present invention has been completed based on these findings.

DISCLOSURE OF THE INVENTION

The present invention provides a preventive agent for fouling organisms, which comprises, as an effective ingredient, at least one compound selected from compounds represented by general formula (1)

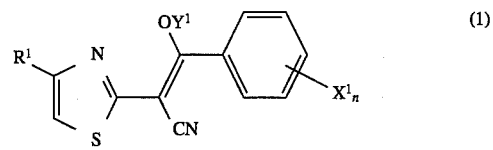

[wherein $R^1$ is a lower alkyl group, or a phenyl group which may be substituted with a halogen atom(s) and/or a lower alkyl group(s); each $X^1$ is a halogen atom; n is an integer of 1–5; when n is 2 or more, $X^1$s may be the same or different; and $Y^1$ is a hydrogen atom or a group —Z—$Y^2$ (Z is a carbonyl group or a sulfonyl group, and $Y^2$ is a substituted or unsubstituted aryl group or a lower alkyl group], or salts thereof; particularly, a preventive agent for fouling organisms, of the above general formula (1) wherein $R^1$ is a tert-butyl group, a phenyl group, a 2-methylphenyl group or a 2-halogenophenyl group; each $X^1$ is a halogen atom bonding to the 2- and/or 6- position of benzene ring; when n is 2 or more, $X^1$s may be the same or different; and $Y^1$ is a hydrogen atom.

BEST MODE FOR CARRYING OUT THE INVENTION

The preventive agent for fouling organisms, according to the present invention is hereinafter described in detail.

The present preventive agent for fouling organisms (hereinafter referred to simply as "present agent" in some cases) contains, as an effective ingredient, at least one compound selected from compounds represented by the above-mentioned general formula (1) or salts thereof (the compounds and salts thereof are hereinafter referred inclusively to simply as "present agent compound" in some cases). The present agent compound is described in Japanese Patent Application Kokai (Laid-Open) No. 154963/1980 or Japanese Patent Application Kokai (Laid-Open) No. 154962/1980, but it has not been known that the compound has an antifouling effect for fouling organisms.

The present agent compound may be any compound of general formula (1) wherein the substituent $R^1$ is a lower alkyl group which may have a straight chain, branched chain and/or alicyclic structure (hereinafter, lower alkyl group has the same definition), or a phenyl group which may be substituted with a lower alkyl group(s) and/or a halogen atom(s) including a chlorine atom(s), a bromine atom(s), an iodine atom(s) and a fluorine atom(s) (hereinafter, halogen atom has the same definition), each $X^1$ is a halogen atom, n is an integer of 1–5, when n is 2 or more, $X^1$s may be the same or different, and $Y^1$ is a hydrogen atom or a group —Z—$Y^2$ (Z is a carbonyl group or a sulfonyl group, and $Y^2$ is a substituted or unsubstituted aryl group or a lower alkyl group); or any salt thereof. When $Y^1$ is a hydrogen atom, specific examples of the present agent compound are as follows.

3-(2-Chlorophenyl)-2-(4-tert-butyl-2,3-dihydrothiazole-2-ylidene)-3-oxopropionitrile 3-(2-Chlorophenyl)-2-(4-phenyl-2,3-dihydrothiazole-2-ylidene)-3-oxopropionitrile 3-(2-Bromophenyl)-2-[4-(2-methylphenyl)-2,3-dihydrothiazole-2-ylidene]-3-oxopropionitrile 3-(2-Iodophenyl)-2-[4-(2-methylphenyl)-2,3-dihydrothiazole-2-ylidene]-3-oxopropionitrile 3-(2-Chlorophenyl)-2-[4-(2-chlorophenyl)-2,3-dihydrothiazole-2-ylidene]-3-oxopropionitrile 3-(2-Chlorophenyl)-2-[4-(2-fluorophenyl)-2,3-dihydrothiazole-2-ylidene]-3-oxopropionitrile 3-(2-Chlorophenyl)-2-[4-(2-chloro-6-fluorophenyl)-2,3-dihydrothiazole-2-ylidene]-3-oxopropionitrile Dimethylammonium salt of 3-(2-chlorophenyl)-2-(4-phenyl-2,3-dihydrothiazole-2-ylidene)-3-oxopropionitrile Dihexylammonium salt of 3-(2-chlorophenyl)-2-(4-phenyl-2,3-dihydrothiazole-2-ylidene)-3-oxopropionitrile Dibutylammonium salt of 3-(2-chlorophenyl)-2-(4-tert-butyl-2,3-dihydrothiazole-2-ylidene)-3-oxopropionitrile When $Y^1$ is a hydrogen atom, the compound represented by general formula (1) takes tautomeric structures as shown below, but this poses no problem for the use of said compound as an effective ingredient for the present preventive agent.

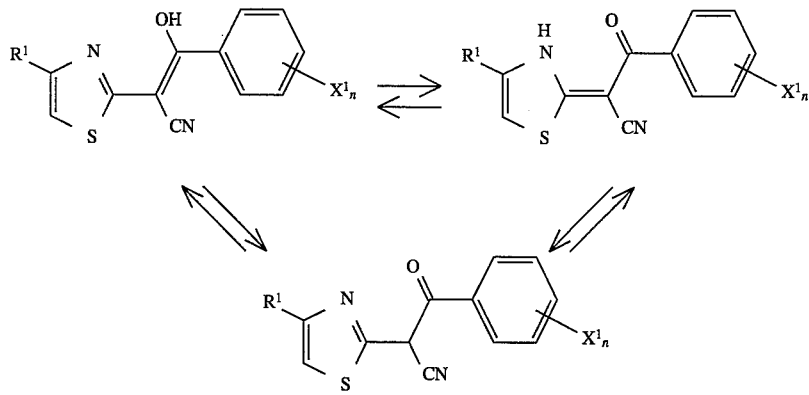

When $Y^1$ is a group —Z—$Y^2$, the present agent compound may be any compound wherein Z is a carbonyl group or a sulfonyl group and $Y^2$ is a substituted or unsubstituted aryl group or a lower alkyl group, or any salt thereof. When Z is a carbonyl group, specific examples of the present agent compound are as follows.

1-(4-Phenyl-thiazole-2-yl)-2-acetoxy-2-(2-chlorophenyl)-acrylonitrile 1-(4-Phenyl-thiazole-2-yl)-2-benzoyloxy-2-(2-chlorophenyl)-acrylonitrile 1-(4-Phenyl-thiazole-2-yl)-2-(2-chlorobenzoyloxy)-2-(2-chlorophenyl)-acrylonitrile 1-(4-Phenyl-thiazole-2-yl)-2-(2-methylbenzoyloxy)-2-(2-chlorophenyl)-acrylonitrile 1-[4-(2-Chlorophenyl)-thiazole-2-yl]-2-acetoxy-2-(2-chlorophenyl)-acrylonitrile 1-[4-(2-Chlorophenyl)-thiazole-2-yl]-2-benzoyloxy-2-(2-chlorophenyl)-acrylonitrile 1-[4-(2-Chlorophenyl)-thiazole-2-yl]-2-(2-chlorobenzoyloxy)-2-(2-chlorophenyl)-acrylonitrile 1-[4-(2-Chlorophenyl)-thiazole-2-yl]-2-(2-methylbenzoyloxy)-2-(2-chlorophenyl)-acrylonitrile 1-[4-(2-Bromophenyl)-thiazole-2-yl]-2-acetoxy-2-(2-chlorophenyl)-acrylonitrile 1-[4-(2-Bromophenyl)-thiazole-2-yl]-2-benzoyloxy-2-(2-chlorophenyl)-acrylonitrile 1-[4-(2-Bromophenyl)-thiazole-2-yl]-2-(2-chlorobenzoyloxy)-2-(2-chlorophenyl)-acrylonitrile 1-[4-(2-Bromophenyl)-thiazole-2-yl]-2-(2-methylbenzoyloxy)-2-(2-chlorophenyl)-acrylonitrile 1-[4-(2-Fluorophenyl)-thiazole-2-yl]-2-acetoxy-2-(2-chlorophenyl)-acrylonitrile 1-[4-(2-Fluorophenyl)-thiazole-2-yl]-2-benzoyloxy-2-(2-chlorophenyl)-acrylonitrile 1-[4-(2-Fluorophenyl)-thiazole-2-yl]-2-(2-chlorobenzoyloxy)-2-(2-chlorophenyl)-acrylonitrile 1-[4-(2-Fluorophenyl)-thiazole-2-yl]-2-(2-methylbenzoyloxy)-2-(2-chlorophenyl)-acrylonitrile 1-(4-Phenyl-thiazole-2-yl)-2-acetoxy-2-(2-chloro-6-fluorophenyl)-acrylonitrile 1-(4-Phenyl-thiazole-2-yl)-2-benzoyloxy-2-(2-chlorophenyl)-acrylonitrile 1-(4-Phenyl-thiazole-2-yl)-2-(2-chlorobenzoyloxy)-2-(2-chloro-6-fluorophenyl)-acrylonitrile 1-(4-Phenyl-thiazole-2-yl)-2-(2-methylbenzoyloxy)-2-(2-chloro-6-fluorophenyl)-acrylonitrile 1-[4-(2-Methylphenyl)-thiazole-2-yl]-2-acetoxy-2-(2-chlorophenyl)-acrylonitrile 1-[4-(2-Methylphenyl)-thiazole-2-yl]-2-benzoyloxy-2-(2-chlorophenyl)-acrylonitrile 1-[4-(2-Methylphenyl)-thiazole-2-yl]-2-(2-chlorobenzoyloxy)-2-(2-chlorophenyl)-acrylonitrile 1-[4-(2-Methylphenyl)-thiazole-2-yl]-2-(2-methylbenzoyloxy)-2-(2-chlorophenyl)-acrylonitrile 1-(4-tert-Butyl-thiazole-2-yl)-2-acetoxy-2-(2-chlorophenyl)-acrylonitrile 1-(4-tert-Butyl-thiazole-2-yl)-2-benzoyloxy-2-(2-chlorophenyl)-acrylonitrile 1-(4-tert-Butyl-thiazole-2-yl)-2-(2-chlorobenzoyloxy)-2-(2-chlorophenyl)-acrylonitrile 1-(4-tert-Butyl-thiazole-2-yl)-2-(2-methylbenzoyloxy)-2-(2-chlorophenyl)-acrylonitrile When Z is a sulfonyl group, specific examples of the present agent compound are as follows.

1-(4-Phenyl-thiazole-2-yl)-2-(methanesulfonyloxy)-2-(2-chlorophenyl)-acrylonitrile 1-(4-Phenyl-thiazole-2-yl)-2-(p-toluenesulfonyloxy)-2-(2-chlorophenyl)-acrylonitrile 1-(4-Phenyl-thiazole-2-yl)-2-(p-benzenesulfonyloxy)-2-(2-chlorophenyl)-acrylonitrile 1-(4-Phenyl-thiazole-2-yl)-2-(n-butanesulfonyloxy)-2-(2-chlorophenyl)-acrylonitrile 1-[4-(2-Chlorophenyl)-thiazole-2-yl]-2-(methanesulfonyloxy)-2-(2-chlorophenyl)-acrylonitrile 1-[4-(2-Chlorophenyl)-thiazole-2-yl]-2-(p-toluenesulfonyloxy)-2-(2-chlorophenyl)-acrylonitrile 1-[4-(2-Chlorophenyl)-thiazole-2-yl]-2-(benzenesulfonyloxy)-2-(2-chlorophenyl)-acrylonitrile 1-[4-(2-Chlorophenyl)-thiazole-2-yl]-2-(n-butanesulfonyloxy)-2-(2-chlorophenyl)-acrylonitrile 1-[4-(2-Bromophenyl)-thiazole-2-yl]-2-(methanesulfonyloxy)-2-(2-chlorophenyl)-acrylonitrile 1-[4-(2-Bromophenyl)-thiazole-2-yl]-2-(p-toluenesulfonyloxy)-2-(2-chlorophenyl)-acrylonitrile 1-[4-(2-Bromophenyl)-thiazole-2-yl]-2-(benzenesulfonyloxy)-2-(2-chlorophenyl)-acrylonitrile 1-[4-(2-Bromophenyl)-thiazole-2-yl]-2-(n-butanesulfonyloxy)-2-(2-chlorophenyl)-acrylonitrile 1-[4-(2-Fluorophenyl)-thiazole-2-yl]-2-(methanesulfonyloxy)-2-(2-chlorophenyl)-acrylonitrile 1-[4-(2-Fluorophenyl)-thiazole-2-yl]-2-(p-toluenesulfonyloxy)-2-(2-chlorophenyl)-acrylonitrile 1-[4-(2-Fluorophenyl)-thiazole-2-yl]-2-(benzenesulfonyloxy)-2-(2-chlorophenyl)-acrylonitrile 1-[4-(2-Fluorophenyl)-thiazole-2-yl]-2-(n-butanesulfonyloxy)-2-(2-chlorophenyl)-acrylonitrile 1-(4-Phenyl-thiazole-2-yl)-2-(methanesulfonyloxy)-2-(2-chloro-6-fluorophenyl)-acrylonitrile 1-(4-Phenyl-thiazole-2-yl)-2-(p-toluenesulfonyloxy)-2-(2-chloro-6-fluorophenyl)-acrylonitrile 1-(4-Phenyl-thiazole-2-yl)-2-(benzenesulfonyloxy)-2-(2-chloro-6-fluorophenyl)-acrylonitrile 1-(4-Phenyl-thiazole-2-yl)-2-(n-butanesulfonyloxy)-2-(2-chloro-6-fluorophenyl)-acrylonitrile 1-[4-(2-Methylphenyl)-thiazole-2-yl]-2-(methanesulfonyloxy)-2-(2-chlorophenyl)-acrylonitrile 1-[4-(2-Methylphenyl)-thiazole-2-yl]-2-(p-toluenesulfonyloxy)-2-(2-chlorophenyl)-acrylonitrile 1-[4-(2-Methylphenyl)-thiazole-2-yl]-2-(benzenesulfonyloxy)-2-(2-chlorophenyl)-acrylonitrile 1-[4-(2-Methylphenyl)-thiazole-2-yl]-2-(n-butanesulfonyloxy)-2-(2-chlorophenyl)-acrylonitrile 1-(4-tert-Butyl-thiazole-2-yl)-2-(methanesulfonyloxy)-2-(2-chlorophenyl)-acrylonitrile 1-(4-tert-Butyl-thiazole-2-yl)-2-(p-toluenesulfonyloxy)-2-(2-chlorophenyl)-acrylonitrile 1-(4-tert-Butyl-thiazole-2-yl)-2-(benzenesulfonyloxy)-2-(2-chlorophenyl)-acrylonitrile 1-(4-tert-Butyl-thiazole-2-yl)-2-(n-butanesulfonyloxy)-2-(2-chlorophenyl)-acrylonitrile The compound of general formula (1) wherein $Y^1$ is a hydrogen atom, can be produced, for example, by reacting a corresponding thiazolylacetonitrile and acid halide in the presence of an organic base as necessary in an inert solvent, as shown in the following reaction formula [see Japanese Patent Application Kokai (Laid-Open) No. 154963/1980]:

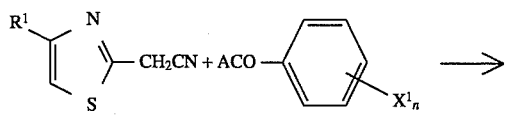

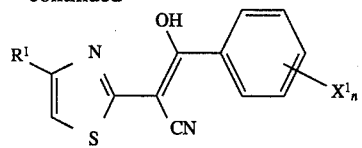

(wherein $R^1$, each $X^1$ and n have the same definitions as given above, and A is a halogen atom).

The compound of general formula (1) wherein $Y^1$ is a group —Z—$Y^2$, can be produced, for example, by reacting the compound obtained by the above reaction formula, with Cl—Z—$Y^2$, as shown in the following reaction formula:

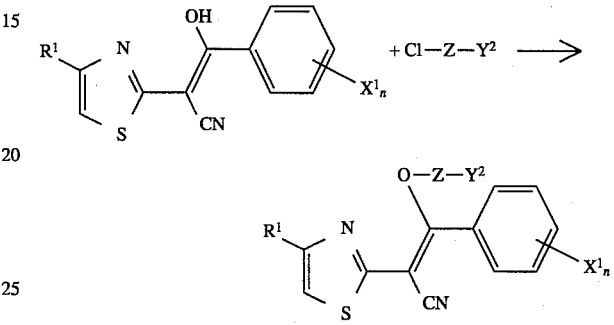

The salt of the compound of general formula (1) can be produced by reacting a compound of general formula (1) with a base such as amine represented by general formula

(wherein $R^2$, $R^3$ and $R^4$ are independently a lower alkyl group which may have a straight-chain, branched chain or cyclic structure, a substituted or unsubstituted phenyl group, an aralkyl group or a hydrogen atom) (said amine includes, for example, alkylamines, dialkylamines, trialkylamines, aniline, benzylamine, phenethylamine and ammonia), nitrogen atom-containing heterocyclic type organic base (e.g. pyridine, morpholine, piperidine or pyrrolidine), alkali metal hydride (e.g. sodium hydride), alkali metal compound (e.g. organic alkali metal compound) or the like [see Japanese Patent Application Kokai (Laid-Open) No. 154962/1980].

The preventive agent for fouling organisms, according to the present invention can be applied in the form of the present agent compound itself. However, the present agent compound can be made into an appropriate form such as coating, solution, emulsion, pellets, flakes or the like depending upon the application purpose and the application site, so that the form can be applied to a variety of sites where the prevention of fouling organisms is required, for example, ship hills, fishing nets, in-sea-water facilities (e.g. buoys), in-water structures (e.g. Part of dam facilities) and feed pipes of cooling water for condenser used in steam power plant or for heat exchanger used in petrochemical plant. When the present preventive agent for fouling organisms is applied to sites which are in constant contact with sea water, for example, ship bottoms, fishing nets, in-sea-water facilities (e.g. buoys), in-water structures (e.g. part of dam facilities) and feed pipes of cooling water for condenser used in steam power plant or for heat exchanger used in petrochemical plant, the present agent compound is generally made into a coating and used as such; as necessary, however, the compound may be made into an emulsion and added as such into said feed pipes of cooling water. Also, the present compound may be molded into pellets by melt molding, compression molding or the like with a hydrophilic resin, a surfactant, etc. and may be placed in a cooling system using sea water.

When the present preventive agent for fouling organisms is prepared in the form of a coating, the present agent compound is compounded with a film-forming agent and, as necessary, a plasticizer, a coloring pigment, an extender pigment and other components generally used in coating preparation; the resulting composition is made into a coating by the use of a stirrer or a conventional dispersing machine (e.g. three-roll mill or sand mill). For example, the present agent compound is compounded with a solvent of aromatic type (e.g. toluene, xylene, cumene or naphtha), alcohol type (e.g. propanol), ketone type (e.g. methyl isobutyl ketone) or the like and a film-forming agent such as oil varnish, synthetic resin (e.g. acrylic resin), synthetic rubber, rosin or the like and, as necessary, a dye, etc., whereby the compound can be made into a coating. The present agent compound is appropriately compounded with a solvent, a film-forming agent, a plasticizer (e.g. Dioctylphthalate (DOP) or chlorinated paraffin), a coloring pigment (e.g. red iron oxide), an extender pigment (e.g. barium sulfonate, talc or zinc white), etc., whereby the compound can be made into a coating. The present agent compound can also be made into an emulsion by compounding with water, a solvent immiscible with water (e.g. the above-mentioned aromatic hydrocarbon) and a known surfactant of anionic type, nonionic type, cationic type or the like. The present agent compound can also be made into pellets or flakes by compounding with a hydrophilic resin (a base material) (e.g. polyethylene glycol which is solid at room temperature) and, as necessary, a plasticizer, a surfactant, etc. and subjecting the resulting composition to melt molding, compression molding or the like.

The amount of the present agent compound used when it is made into a desired form, is appropriately determined depending upon the application purpose, the kind of form, the application method, etc. The amount has no restriction as long as the present agent compound can be made into an intended form. However, when the present agent compound is made into, for example, a coating, a solution, an emulsion or the like, the compound can be used in an amount of generally 1–40% by weight, preferably 3–20% by weight; when the compound is made into pellets or the like, the compound can be used in an amount of generally 30–95% by weight, preferably 50–90% by weight. The other components used in the present agent may be those components generally used in individual forms, and their kinds, combinations, amounts, etc. not only can be those shown in the present specification but also can be appropriately varied in wide ranges so as to obtain an agent of intended properties, etc.

The present preventive agent for fouling organisms can be applied using a method appropriately selected from ordinary application methods such as coating, spraying, impregnation, addition to water, placing in water and the like, depending upon the application site, the application purpose and the form of agent. That is, the present preventive agent for fouling organisms, when used, for example, as a coating, can be applied to a ship hill, a fishing net, an in-water structure, a water feed pipe, etc. by coating, spraying or the like. When a fishing net is an object, the fishing net can be immersed in the present preventive agent for fouling organisms which is in the form of a coating or a solution, to coat and/or impregnate the fishing net with said agent; this is an example of effective application of the present agent to fishing net. When a water feed pipe is an object, the present agent can be applied, for example, by adding the present agent to water in the form of a solution or an emulsion, or by fixing the present agent in the form of pellets or flakes by a known means (e.g. suspension or attaching) appropriately selected depending upon the actual site situation. Also, the present agent compound may be incorporated into, for example, ropes or fibrous materials (these are raw materials of fishing net, etc.) during their production to endow the ropes or fibrous materials with a preventive activity for fouling organisms; in this case, the present agent compound can be used in or by a form and a method both other than mentioned above.

The present agent compound, which is an effective ingredient of the present preventive agent for fouling organisms, is particularly effective for prevention of fouling by animal periphytons. Therefore, its use as necessary in combination with other chemicals which are effective for prevention of fouling sea weeds, is useful. The present agent compound may also be used in combination with other organic chemical in order to increase the antifouling effect or the antifouling duration. The organic chemical used for such purposes can be exemplified by substituted phenylmaleimides (e.g. 2,3-dichloro-N-2',6'-diethylphenylmaleimide and 2,4,6-trichlorophenylmaleimide), tetramethylthiuram disulfide, tetramethylthiuram disulfide, zinc dimethyldithiocarbamate, dizinc bis-(dimethyldithiocarbamate), ethylenebis(dithiocarbamate), tetra-chloroisophthalonitrile, 2-thiocyanomethylthiobenzothiazole, 3,4-dichlorophenyl isothiocyanate, 4,5-dichloro-2-n-octyl-3 (2H) isothiazolone, 3-(3,4-dichlorophenyl)-1,1-dimethylurea (DCMU), 2- methylthio-4-tert-butylamino-6-cyclopropylamino-S-triazine, p-nonylphenol, zinc pyrithione, N,N-dimethyl-N'-phenyl-N'-(fluorodichloromethylthio) sulfamide, 2,3,5,6-tetrachloro-4-(methylsulfanyl)-pyridine, tetraphenylboron=pyridinium and triphenylboron=pyridinum. These organic chemicals can be used singly or in admixture of two or more kinds.

The present preventive agent for fouling organisms may be used with a copper compound such as cuprous oxide, copper rhodanide or the like. In this case, for example, a coating can be made using the same components as mentioned above, by the same method as mentioned above. Further, the present preventive agent may be used with a silicone resin, a silicone oil or the like.

Incidentally, the present agent compound used as an effective ingredient of the present preventive agent for fouling organisms has high safety, and 3-(2-chlorophenyl)-2-(4-phenyl-2,3-dihydrothiazole-2-ylidene)-3-oxopropionitrile (which is an example of the present agent compound and which was used in Test 2 shown later) gives a $LD_{50}$ of 5,000 mg/kg or more in oral acute toxicity test for rat and is negative in mutagenicity test.

The present invention is hereinafter described more specifically by way of Test Examples, Compounding Examples, etc. However, the present invention is in no way restricted by them.

Synthesis 1 of present agent compounds

In a 2-liter reaction flask equipped with a thermometer, a Dimroth condenser, a dropping funnel and a stirrer were placed 153.2 g of 2-cyanomethyl-4-phenyl-thiazole and 500 ml of toluene. The mixture was cooled to 10°–20° C., and thereto was added 154.5 g of triethylamine, followed by dropwise addition of 133.9 g of 2-chlorobenzoylchloride. After the completion of the dropwise addition, 0.45 g of 4-(N,N-dimethylamino)pyridine was added. The mixture was aged at room temperature for 10 hours. Then, 10% hydrochloric acid was added for precipitation. The precipitated solid was collected by filtration, and the crystals were washed with 675 ml of toluene and 585 ml of water to obtain 160 g (yield: 52%) of an intended product, i.e. 3-(2-chlorophenyl)-2-(4-phenyl-2,3-dihydrothiazole-2-ylidene)-3-oxopropionitrile.

Compounds shown in Table 1 were obtained in a similar manner.

Tests 1–10

The nauplii of *Balanus amphitrite*, hatched in a natural sea water sterilized by filtration were tamed with a diatom feed to convert them into cypris larvae (settling stage larvae). Ten of these cypris larvae and 4 ml of a natural sea water sterilized by filtration were placed in a laboratory dish having a diameter of 3 cm. 10 mg of a present agent compound was made into 1 g of an emulsion with an emulsifier consisting of cyclohexanone and Tween 80 (a trade name of Kao Atlas Co., Ltd.), and the emulsion was diluted to a given concentration of present agent compound with an artificial sea water. 1 ml of the diluted solution was added into the above laboratory dish. The laboratory dish was allowed to stand in a thermostat of 20° C. for 24 hours, and the number of dead cypris larvae was examined. This test was repeated three times, and the mortality rate of *Balanus amphitrite* at a given concentration of present agent compound was determined. The results are shown in Table 1.

Blank Test

A test for mortality rate was conducted in the same manner as in Test 1 except that no present agent compound was used. The result is shown in Table 1.

Comparative Test 1

A test for mortality rate was conducted in the same manner as in Test 1 except that bis(tributyltin) oxide (hereinafter referred to simply as "TBTO" in some cases) was used as a test compound in place of the present agent compound. The result is shown in Table 1.

TABLE 1

| Test No. | Present agent compound | | | Mortality rate(%) (0.1 ppm) |
|---|---|---|---|---|
| | $Y^1$ | $R^1$ | $X^1_n$ | |
| 1 | H | phenyl | 2-Cl | 100 |
| 2 | H | $-C(CH_3)_3$ | 2-Cl | 100 |
| 3 | H | 2-methylphenyl | 2-Br | 100 |
| 4 | H | 2-methylphenyl | 2-I | 100 |
| 5 | H | 2-chlorophenyl | 2-Cl | 100 |
| 6 | H | 2-fluorophenyl | 2-Cl | 100 |
| 7 | H | 2-fluorophenyl | 2-Cl, 6-F | 100 |
| 8* | H | phenyl | 2-Cl | 100 |
| 9* | H | phenyl | 2-Cl | 100 |
| 10* | H | $-C(CH_3)_3$ | 2-Cl | 100 |
| Blank test | — | — | — | 0 |
| Comparative test | | TBTO | | 50 |

*Test 8 used a dimethylamine salt; Test 9 used a dihexylamine salt; and Test 10 used a dibutylamine salt.

Compounding 1

Components including the present agent compound used in Test 1 were compounded in the proportions shown in the following Table 2 and then dispersed down to 50 microns using a small attritor for laboratory use to obtain an preventive agent for fouling organisms, in the form of a coating.

TABLE 2

| Component | Ratio (wt. %) |
|---|---|
| Present agent compound (used in Test 1) | 5 |
| 2-Methylthio-4-tert-butylamino-6-cyclopropyl-s-triazine | 15 |
| Aroprene R-10 (chlorinated rubber resin, a product of ICI) | 10 |
| Rosin | 7 |
| Dioctyl phthalate | 1 |
| Red iron oxide | 10 |
| Talc | 10 |
| Barium sulfate | 10 |
| Zinc white | 6 |
| Shellsol A (a product of Shell Kagaku K.K.) | 26 |

Compounding 2

Components including the present agent compound used in Test 17 described later were compounded in the following proportions, followed by dispersion and dissolution to obtain a preventive agent for fouling organisms, in the form of a solution.

| Present agent compound | 10 wt. % |
|---|---|
| Xylene | 70 wt. % |
| Acrylic resin | 20 wt. % |

Compounding 3

The following components including the present agent compound used in Test 2 were prepared in the following proportions. The polyethylene glycol was melted and the present agent compound was dispersed therein. The dispersion was molded to obtain a preventive agent for fouling organisms, in the form of pellets.

| | |
|---|---|
| Present agent compound | 85 wt. % |
| Polyethylene glycol (average molecular weight: 1,540) | 15 wt. % |

Test 11 (antifouling effect in field immersion test)

The preventive agent for fouling organisms, obtained in Compounding 1 was brush-coated, two times in an amount of 5 g per one time, on a FRP plate (30 cm×10 cm×0.3 cm) which had been subjected to sufficient washing with xylene for removal of resins such as releasant and the like, whereby a test plate was prepared. The test plate was encased in an iron frame, then suspended in sea water from a raft, and kept at a depth of 1.5 m. The test plate was pulled up after 1, 3 and 6 months to observe the condition of settlement of fouling organisms. The results are shown in Table 3. Incidentally, the condition of settlement of fouling organisms was expressed according to the following criterion.

—: settlement area is less than 1%.

+: settlement area is 1% to less than 10%.

++: settlement area is 10% to less than 30%.

+++: settlement area is 30% or more.

Test 12 (antifouling effect in field immersion test)

An in-sea-water immersion test was conducted in the same manner as in Test 11 except that the present agent compound used in preventive agent for fouling organisms was changed from the compound used in Test 1 to the compound used in Test 2. The results are shown in Table 3. Incidentally, the condition of settlement of fouling organisms was evaluated and expressed in the same manner as in Test 11.

Comparative Test 2

An in-sea-water immersion test was conducted in the same manner as in Test 11 except that a FRP plate not coated with any preventive agent for fouling organisms was used as a test plate. The results are shown in Table 3. Incidentally, the condition of settlement of fouling organisms was evaluated and expressed in the same manner as in Test 11.

Comparative Test 3

An in-sea-water immersion test was conducted in the same manner as in Test 11 except that a FRP plate coated with a coating which was the preventive agent for fouling organisms, of Compounding 1 minus the present agent compound, was used as a test plate. The results are shown in Table 3. Incidentally, the condition of settlement of fouling organisms was evaluated and expressed in the same manner as in Test 11.

TABLE 3

| | Settlement condition | | | | | |
|---|---|---|---|---|---|---|
| | 1 month | | 3 months | | 6 months | |
| Test | Animals | Algae | Animals | Algae | Animals | Algae |
| Test 11 | — | — | — | — | — | — |
| Test 12 | — | — | — | — | — | — |
| Comparative Test 2 | ++ | ++ | +++ | +++ | +++ | + |
| Comparative Test 3 | ++ | — | +++ | — | +++ | — |

Note: Site for in-sea-water immersion test: Orido Bay, Shimidzu City, Shizuoka Prefecture, Japan As seen in Table 3, the preventive agents for fouling organisms, according to the present invention showed sufficient effects.

Synthesis 2 of present agent compounds

In a reaction flask equipped with a thermometer, a Dimroth condenser, a stirrer and a dropping funnel were placed 6.8 g (0.02M) of the present agent compound used in Test 2, 50 ml of acetone and 3.2 g (0.03M) of sodium carbonate. To the mixture being stirred was dropwise added, from the dropping funnel, a solution of 1.73 g (0.022M) of acetyl chloride dissolved in 10 ml of acetone. After the completion of the dropwise addition, a reaction was conducted at the same temperature for 4–10 hours. After the completion of the reaction, the reaction mixture was poured into ice water. The oil layer was extracted with toluene. The toluene layer was washed with water, dried over anhydrous sodium sulfate, and subjected to distillation under reduced pressure to remove toluene. The residue was a light brown oily material. The oily material solidified when allowed to stand at room temperature. The resulting solid was recrystallized from ethyl acetate to obtain 5.5 g (yield: 72%) of an intended product, i.e. 1-(4-phenyl-thiazole-2-yl)-2-acetoxy-2-(2-chlorophenyl)-acrylonitrile.

Compounds shown in Table 4 were obtained in the same manner.

Tests 13–16

Tests for mortality rate were conducted in the same manner as in Tests 1–10 except that the present agent compounds were changed to those shown in Table 4. The results are shown in Table 4.

TABLE 4

| Test No. | Present agent compound | | | | Mortality rate(%) |
|---|---|---|---|---|---|
| | Z | Y¹ Y² | R¹ | X¹ₙ | |
| 13 | —CO | $CH_3$ | 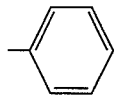 | 2-chloro | 100 |
| 14 | —CO | 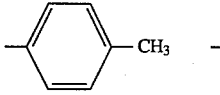—$CH_3$ | 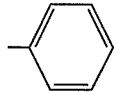 | 2-chloro | 100 |
| 15 | —CO | n-$C_4H_9$ | 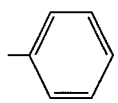 | 2-chloro | 100 |
| 16 | —CO |  | 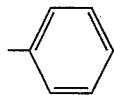 | 2-chloro | 100 |

Synthesis 3 of present agent compounds

In a reaction flask equipped with a thermometer, a Dimroth condenser, a stirrer and a dropping funnel were placed 6.8 g (0.02M) of the present agent compound used in Test 2, 50 ml of acetone and 3.2 g (0.03M) of sodium carbonate. To the mixture being stirred was dropwise added, at room temperature from the dropping funnel, a solution of 4.2 g (0.022M) of p-toluenesulfonyl chloride dissolved in 10 ml of acetone. After the completion of the dropwise addition, a reaction was conducted at the same temperature for 4–10 hours. After the completion of the reaction, the reaction mixture was poured into ice water. The oil layer was extracted with toluene. The toluene layer was washed with water, dehydrated, and subjected to distillation under reduced pressure to remove toluene. The residue was a light brown oily material. The oily material crystallized when allowed to stand. The resulting crystals were recrystallized from ethyl acetate to obtain 5 g (yield: 50.5%) of an intended product, i.e. 1-(4-Phenyl-thiazole-2-yl)-2-(p-toluenesulfonyloxy)-2-(2-chlorophenyl)-acrylonitrile.

Other compounds could be obtained in the same manner. The results are shown in Table 5 ($R^1$ and $X^1_n$ are the same as in Table 4 of Synthesis 2).

TABLE 5

| Synthesis No. | Y¹ | | Yield (%) | Melting point (°C.) |
|---|---|---|---|---|
| | Z | Y² | | |
| 3 | —$SO_2$ | 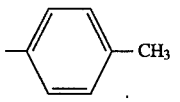—$CH_3$ | 50.5 | 174–176 |
| 4 | —$SO_2$ | $CH_3$ | 52.8 | 98–103 |
| 5 | —$SO_2$ | n-$C_4H_9$ | 68.5 | 102–108 |
| 6 | —$SO_2$ | 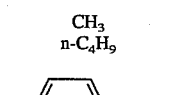—$CH_3$ | 78.1 | 192–195 |

Tests 17–20

Tests for mortality rate were conducted in the same manner as in Tests 1–10 except that the present agent compounds were changed to those shown in Table 6. The results are shown in Table 6 ($R^1$ and $X^1_n$ are the same as in Table 4 of Synthesis 2).

TABLE 6

| Test No. | Y¹ | | Mortality Rate (%) |
|---|---|---|---|
| | Z | Y² | |
| 17 | —$SO_2$ | $CH_3$ | 100 |
| 18 | —$SO_2$ | 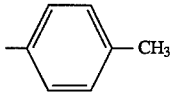—$CH_3$ | 100 |
| 19 | —$SO_2$ | n-$C_4H_9$ | 100 |
| 20 | —$SO_2$ | 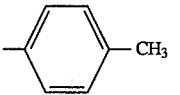 | 100 |

Industrial Applicability

The preventive agent for fouling organisms, according to the present invention contains a compound(s) other than organotin compounds as an effective ingredient, has high safety, prevents settlement of fouling organisms to ships, in-water structures, fishing nets, etc. at a low effective ingredient content, and exhibits an antifouling effect stably over a long period of time.

We claim:

1. A compound for inhibiting growth of fouling organisms on structures in contact with water, which is a compound of the formula:

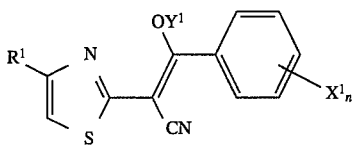

wherein $R^1$ is a lower alkyl group, or a phenyl group which is unsubstituted or substituted by halogen or lower alkyl or both; each $X^1$ is a halogen atom; n is an integer of 1 to 5, with the proviso that when n is 2 or more, each $X^1$ is the same or different; and $Y^1$ is a group of the formula $—Z—Y^2$, wherein Z is sulfonyl and $Y^2$ is unsubstituted aryl or aryl substituted by a lower alkyl group, or a salt thereof.

2. The compound of claim 1, wherein $R^1$ is selected from the group consisting of tert-butyl, phenyl, 2-methylphenyl and 2-halogenophenyl.

3. The compound of claim 1, wherein $X^1$ is a halogen atom bonded to the 2- or 6- position of the benzene ring or both.

4. The compound of claim 1, which is selected from the group consisting of 1-(4-phenyl-thiazole-2-yl)-2-(methanesulfonyloxy)-2-(2-chlorophenyl)-acrylonitrile, 1-(4-phenyl-thiazole-2-yl)-2-(p-toluenesulfonyloxy)-2-(2-chlorophenyl)-acrylonitrile, 1-(4-phenyl-thiazole-2-yl)-2-(p-benzenesulfonyloxy)-2-(2-chlorophenyl)-acrylonitrile), 1-(4-phenyl-thiazole-2-yl)-2-(n-butanesulfonyloxy)-2-(2-chlorophenyl)-acrylonitrile, 1-(4-(2-chlorophenyl)-thiazole-2-yl)-2-(methanesulfonyloxy)-2-(2-chlorophenyl)-acrylonitrile, 1-(4-(2-chlorophenyl)-thiazole-2-yl)-2-(p-toluenesulfonyloxy)-2-(2-chlorophenyl)-acrylonitrile, 1-4-(2-chlorophenyl)-thiazole-2-yl)-2-(benzenesulfonyloxy)-2-(2-chlorophenyl)-acrylonitrile, 1-(4-(2-chlorophenyl)-thiazole-2-yl)-2-(n-butanesulfonyloxy)-2-(2-chlorophenyl)-acrylonitrile, 1-(4-(2-bromophenyl)-thiazole-2-yl)-2-(methanesulfonyloxy)-2-(2-chlorophenyl)-acrylonitrile, 1-(4-(2-bromophenyl)-thiazole-2-yl)-2-(p-toluenesulfonyloxy)-2-(2-chlorophenyl)-acrylonitrile, 1-(4-(2-bromophenyl)-thiazole-2-yl)-2-(benzenesulfonyloxy)-2-(chlorophenyl)-acrylonitrile, 1-(4-(2-bromophenyl)-thiazole-2-yl)-2-(n-butanesulfonyloxy)-2-(2-chlorophenyl)-acrylonitrile, 1-(4-(2-fluorophenyl)-thiazole-2-yl)-2-(methanesulfonyloxy)-2-(2-chlorophenyl)-acrylonitrile, 1-(4-(2-fluorophenyl)-thiazole-2-yl)-2-(p-toluenesulfonyloxy)-2-(2-chlorophenyl)-acrylonitrile, 1-(4-(2-fluorophenyl)-thiazole-2-yl)-2-(benzenesulfonyloxy)-2-(2-chlorophenyl)-acrylonitrile, 1-(4-(2-fluorophenyl)-thiazole-2-yl)-2-(n-butanesulfonyloxy)-2-(2-chlorophenyl)-acrylonitrile, 1-(4-phenyl-thiazole-2-yl)-2-(methanesulfonyloxy)-2-(2-chloro-6-fluorophenyl)-acrylonitrile, 1-(4-phenyl-thiazole-2-yl)-2-(p-toluenesulfonyloxy)-2-(2-chloro-6-fluorophenyl)-acrylonitrile, 1-(4-phenyl-thiazole-2-yl)-2-(benzenesulfonyloxy)-2-(2-chloro-6-fluorophenyl)-acrylonitrile, 1-(4-phenyl-thiazole-2-yl)-2-(n-butanesulfonyloxy)-2-(2-chloro-6-fluorophenyl)-acrylonitrile, 1-(4-(2-methylphenyl)-thiazole-2-yl)-2-(methanesulfonyloxy)-2-(2-chlorophenyl)-acrylonitrile, 1-(4-(2-methylphenyl)-thiazole-2-yl)-2-(p-toluenesulfonyloxy)-2-(2-chlorophenyl)-acrylonitrile, 1-(4-(2-methylphenyl)-thiazole-2-yl)-2-(benzenesulfonyloxy)-2-(2-chlorophenyl)acrylonitrile, 1-(4-(2-methylphenyl)-thiazole-2-yl)-2-(n-butanesulfonyloxy-2-(2-chlorophenyl)-acrylonitrile, 1-(4-tert-butyl-thiazole-2-yl)-2-(methanesulfonyloxy)-2-(2-chlorophenyl)-acrylonitrile, 1-)4-tert-butyl-thiazole-2-yl)-2-(p-toluenesulfonyloxy)-2-(2-chlorophenyl)-acrylonitrile, 1-(4-tert-butyl-thiazole-2-yl)-2-(benzenesulfonyloxy)-2-(2-chlorophenyl)-acrylonitrile, 1-(4-tert-butyl-thiazole-2-yl)-2-(benzenesulfonyloxy)-2-(2-chlorophenyl)-acrylonitrile and 1-(4-tert-butyl-thiazole-2-yl)-2-(n-butanesulfonyloxy)-2-(2-chlorophenyl)-acrylonitrile.

5. A composition for inhibiting growth of fouling organisms on structures in contact with water, which comprises:

a) one or more compounds having the formula:

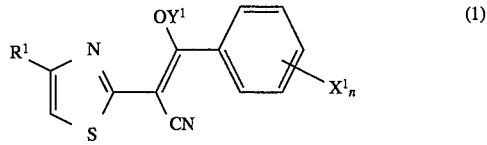

wherein $R^1$ is lower alkyl, or phenyl which is unsubstituted or substituted by halogen or lower alkyl or both; each $X^1$ is a halogen atom; n is an integer of 1 to 5, with the proviso that when n is 2 or more, each $X^1$ is the same or different; and $Y^1$ is a group of the formula $—Z—Y^2$, wherein Z is sulfonyl and $Y^2$ is unsubstituted aryl or aryl substituted by a lower alkyl group, or a salt thereof; and b) a suitable carrier agent.

6. The composition of claim 5, wherein in said one or more compounds (a), $R^1$ is selected from the group consisting of tert-butyl, phenyl, 2-methylphenyl and 2-halogenphenyl.

7. The composition of claim 5, wherein in said one or more compounds (a), each $X^1$ is a halogen atom bonded to the 2- or 6- position of the benzene ring or both.

8. The composition of claim 6, wherein said one or more compounds a) are selected from the group consisting of 1-(4-phenyl-thiazole-2-yl)-2-(methanesulfonyloxy)-2-(2-chlorophenyl)-acrylonitrile, 1-(4-phenyl-thiazole-2-yl)-2-(p-toluenesulfonyloxy)-2-(2-chlorophenyl)-acrylonitrile, 1-(4-phenyl-thiazole-2-yl)-2-(p-benzenesulfonyloxy)-2-(2-chlorophenyl)-acrylonitrile), 1-(4-phenyl-thiazole-2-yl)-2-(n-butanesulfonyloxy)-2-(2-chlorophenyl)-acrylonitrile, 1-(4-(2-chlorophenyl)-thiazole-2-yl)-2-(methanesulfonyloxy)-2-(2-chlorophenyl)-acrylonitrile, 1-(4-(2-chlorophenyl)-thiazole-2-yl)-2-(p-toluenesulfonyloxy)-2-(2-chlorophenyl)-acrylonitrile, 1-(4-(2-chlorophenyl)-thiazole-2-yl)-2-(benzenesulfonyloxy)-2-(2-chlorophenyl)-acrylonitrile, 1-(4-(2-chlorophenyl)-thiazole-2-yl)-2-(n-butanesulfonyloxy)-2-(2-chlorophenyl)-acrylonitrile, 1-(4-(2-bromophenol)-thiazole-2-yl)-2-(methanesulfonyloxy)-2-(2-chlorophenyl)-acrylonitrile, 1-(4-(2-bromophenol)-thiazole-2-yl)-2-(p-toluenesulfonyloxy)-2-(2-chlorophenyl)-acrylonitrile, 1-(4-(2-bromophenol)-thiazole-2-yl)-2-(benzenesulfonyloxy)-2-(chlorophenyl)-acrylonitrile, 1-(4-(2-bromophenol)-thiazole-2-yl)-2-(butanesulfonyloxy)-2-(2-chlorophenyl)-acrylonitrile, 1-(4-(2-fluorophenyl)-thiazole-2-yl)-2-(methanesulfonyloxy)-2-(2-chlorophenyl)-acrylonitrile, 1-(4-(2-fluorophenyl)-thiazole-2-yl)-2-(p-toluenesulfonyloxy)-2-(2-chlorophenyl)-acrylonitrile, 1-(4-(2-fluorophenyl)-thiazole-2-yl)-2-(benzenesulfonyloxy)-2-(2-chlorophenyl)-acrylonitrile, 1-(4-(2-fluorophenyl)-thiazole-2-yl)-2-(n-butanesulfonyloxy)-2-(2-chlorophenyl)-acrylonitrile, 1-(4-phenyl-thiazole-2-yl)-2-(methanesulfonyloxy)-2-(2-chloro-6-fluorophenyl)-acrylonitrile, 1-(4-phenyl-thiazole-2-yl)-2-(p-toluenesulfonyloxy)-2-(2chloro-6-fluorophenyl)-acrylonitrile, 1-(4-phenyl-thiazole-2-yl)-2-(benzenesulfonyloxy)-2-(2-chloro-6-fluorophenyl)-acrylonitrile, 1-(4-phenyl-thiazole-2-yl)-2-(n-butanesulfonyloxy)-2-(2-chloro-6-fluorophenyl)-acrylonitrile, 1-(4-(2-methylphenyl)-thiazole-2-yl)2-(methanesulfonyloxy)-2-(2-chlorophenyl)-acrylonitrile, 1-(4-(2-methylphenyl)-thiazole-2-yl)-2-(p-toluenesulfonyloxy)-2-(2-chlorophenyl)-acrylonitrile, 1-(4-(2-methylphenyl)-thiazole-2-yl)-2-(benzenesulfonyloxy)-2-(2-chlorophenyl)acrylonitrile, 1-(4-(2-methylphenyl)-thiazole-2-yl)-2-(n-butanesulfonyloxy)-2-(2-chlorophenyl)-acrylonitrile, 1-(4-tert-butyl-thiazole-2-yl)-2-(methanesulfonyloxy)-2-(2-chlorophenyl)-acrylonitrile, 1-(4-tert-butyl-thiazole-2-yl)-2-(p-toluenesulfonyloxy)-2-(2-chlorophenyl)-acrylonitrile, 1-(4-tert-butyl-thiazole-2-yl)-2-(benzenesulfonyloxy)-2-(2-chlorophenyl)-acrylonitrile, 1-(4-tert-butyl-thiazole-2-yl)-2-(benzenesulfonyloxy)-2-(2-chlorophenyl)-acrylonitrile and 1-(4-tert-butyl-thiazole-2-yl)-2-(n-butanesulfonyloxy)-2-(2-chlorophenyl)-acrylonitrile.

9. The composition of claim 6, which is in a form of a coating, solution, emulsion, pellets or flakes.

10. The composition of claim 9, which is in the form of a coating, solution or emulsion, and comprises about 1 to 40% by wt. of the one or more compounds a) based upon the total weight of the compostiion.

11. The composition of claim 10, which contains about 3 to 20% by wt. of the one or more compounds a).

12. The composition of claim 9, which is in the form of pellets or flakes, and comprises about 35 to 95% by wt. of the one or more compounds a) based upon the total weight of the composition.

13. The composition of claim 12, which contains about 50 to 90% by wt. of the one or more compounds a).

* * * * *

UNITED STATES PATENT AND TRADEMARK OFFICE
CERTIFICATE OF CORRECTION

PATENT NO. : 5,603,755
DATED : February 18, 1997
INVENTOR(S) : Hideo OKADA, et al.

It is certified that error appears in the above-indentified patent and that said Letters Patent is hereby corrected as shown below:

On the title page, Item [54] and the top of Column 1, the title should read:

--PREVENTIVE AGENT FOR FOULING ORGANISMS--

Signed and Sealed this

Twentieth Day of May, 1997

Attest:

BRUCE LEHMAN

Attesting Officer

Commissioner of Patents and Trademarks